(12) United States Patent
Perez-Cruet et al.

(10) Patent No.: US 7,892,265 B2
(45) Date of Patent: Feb. 22, 2011

(54) SURGICAL SCREW INCLUDING A BODY THAT FACILITATES BONE IN-GROWTH

(75) Inventors: Miquelangelo J. Perez-Cruet, Bloomfield, MI (US); John R. Pepper, Cheshire, CT (US); John A. Miller, Bloomfield Village, MI (US)

(73) Assignee: Mi4spine, LLC, Bloomfield Hills, MI (US)

(*) Notice: Subject to any disclaimer, the term of this patent is extended or adjusted under 35 U.S.C. 154(b) by 633 days.

(21) Appl. No.: 11/679,780

(22) Filed: Feb. 27, 2007

(65) Prior Publication Data
US 2008/0177331 A1 Jul. 24, 2008

Related U.S. Application Data

(63) Continuation-in-part of application No. 11/646,750, filed on Dec. 28, 2006, now Pat. No. 7,666,211.

(51) Int. Cl.
*A61B 17/04* (2006.01)
*A61B 17/84* (2006.01)
*A61F 2/08* (2006.01)

(52) U.S. Cl. .................. 606/300; 606/301; 606/314

(58) Field of Classification Search ......... 606/300–321, 606/76, 246–279; 411/82.2, 257, 258, 900–903, 411/930
See application file for complete search history.

(56) References Cited

U.S. PATENT DOCUMENTS

| | | | |
|---|---|---|---|
| 4,931,055 A | 6/1990 | Bumpus et al. | |
| 5,047,029 A | 9/1991 | Aebi et al. | |
| 5,258,044 A * | 11/1993 | Lee | 623/66.1 |
| 5,360,431 A | 11/1994 | Puno et al. | |
| 5,360,448 A * | 11/1994 | Thramann | 606/60 |
| 5,545,166 A | 8/1996 | Howland | |
| 5,613,968 A | 3/1997 | Lin | |
| 5,628,740 A | 5/1997 | Mullane | |
| 5,688,275 A | 11/1997 | Koros et al. | |
| 5,702,393 A | 12/1997 | Pfaifer | |
| 5,733,284 A | 3/1998 | Martin | |
| 5,782,831 A | 7/1998 | Sherman et al. | |
| 6,241,730 B1 | 6/2001 | Alby | |
| 6,267,764 B1 | 7/2001 | Elberg | |
| 6,641,583 B2 | 11/2003 | Shluzas et al. | |
| 6,866,666 B1 * | 3/2005 | Sinnott et al. | 606/302 |
| 6,887,242 B2 | 5/2005 | Doubler et al. | |
| 7,083,621 B2 | 8/2006 | Shaolian et al. | |

(Continued)

*Primary Examiner*—Eduardo C Robert
*Assistant Examiner*—Christina Negrelli
(74) *Attorney, Agent, or Firm*—John A. Miller; Miller IP Group, PLC

(57) ABSTRACT

A surgical screw that includes a body portion that facilitates bone in-growth from a bone in which the screw is mounted so as to stabilize the screw in the bone. The body portion can have various configurations for facilitating bone in-growth, such as indentations, a roughened surface, such as by acid etching or abrasive media blasting, specialized coatings, such as hydroxyapetite, sintered beads, machined channels, etc. Because the body portion of the screw facilitates bone growth, the screw will be more firmly mounted to the bone so as to have a greater integrity in response to movement of the bone. The type of surgical screw can be any surgical screw that will benefit from being better anchored in bone, such as pedicle screws, long bone screws, cervical fusion screws, tendon anchoring screws, etc.

10 Claims, 6 Drawing Sheets

U.S. PATENT DOCUMENTS

| | | |
|---|---|---|
| 2003/0009226 A1 | 1/2003 | Graf |
| 2003/0220643 A1 | 11/2003 | Ferree |
| 2004/0049279 A1 | 3/2004 | Sevrain |
| 2004/0116927 A1 | 6/2004 | Graf |
| 2005/0004674 A1 | 1/2005 | Senegas et al. |
| 2005/0038433 A1 | 2/2005 | Young |
| 2005/0065514 A1 | 3/2005 | Studer |
| 2005/0113929 A1* | 5/2005 | Cragg et al. ............. 623/17.16 |
| 2005/0165396 A1 | 7/2005 | Fortin et al. |
| 2006/0079896 A1 | 4/2006 | Kwak et al. |
| 2006/0111715 A1* | 5/2006 | Jackson ...................... 606/61 |
| 2006/0155286 A1* | 7/2006 | Wang .......................... 606/73 |
| 2006/0189983 A1 | 8/2006 | Fallin et al. |
| 2006/0189984 A1 | 8/2006 | Fallin et al. |
| 2006/0212033 A1 | 9/2006 | Rothman et al. |

\* cited by examiner

SURGICAL SCREW INCLUDING A BODY THAT FACILITATES BONE IN-GROWTH

CROSS-REFERENCE TO RELATED APPLICATIONS

This application is a continuation-in-part application of U.S. patent application Ser. No. 11/646,750, filed Dec. 28, 2006, titled "Vertebral Disc Annular Fibrosis Tensioning and Lengthening Device."

BACKGROUND OF THE INVENTION

1. Field of the Invention

This invention relates generally to a surgical screw and, more particularly, to a surgical screw that includes a body portion that facilitates bone in-growth.

2. Discussion of the Related Art

The human spine includes a series of vertebrae interconnected by connective tissue referred to as intervertebral discs that act as a cushion between the vertebrae. The discs allow for movement of the vertebrae so that the back can bend and rotate.

The intervertebral disc is an active organ in which the normal and pathologic anatomies are well known, but the normal and pathologic physiologies have not been greatly understood. The intervertebral disc permits rhythmic motions required of all vertebrate animals in their various forms of locomotion. The disc is a high-pressure system composed primarily of absorbed water, an outer multilayered circumferential annulus of strong, flexible, but essentially inelastic collagen fibers, and an inner core of a hydrogel called the nucleus pulposus. The swelling of the contained hydrogel creates the high pressure that tightens the annular fibers and its laminations. Degeneration of discs in humans is typically a slow, complex process involving essentially all of the mechanical and physiologic components with loss of water holding capacity of the disc. Discogenic pain arises from either component, but is primarily due to altered chemistry. When this pain is severely disabling and unyielding, the preferred contemporary treatments are primarily surgical, particularly fusion and/or disc replacement.

Annular collagen fibers are arranged in circumferential belts or laminations inserting strongly and tangentially in right- and left-handed angulated patches into each adjacent vertebral body. Inside the annular ring is contained an aggrecan, glycosaminoglycan, a protein-sugar complex gel having great hygroscopic ability to hold water. The swelling pressure of this gel of the nucleus maintains the pressure within the annulus, forcing the vertebrae apart and tightening the annular fibers. This tightening provides the primary mechanical stability and flexibility of each disc of the spinal column. Further, the angulated arrangement of the fibers also controls the segmental stability and flexibility of the motion segment. Therefore, the motion of each segment relates directly to the swelling capacity of the gel and secondarily to the tightness of intact annulus fibers. The same gel is also found in thin layers separating the annular laminar construction, providing some apparent elasticity and separating the laminations, reducing interlaminar torsional abrasion. With aging or degeneration, nucleus gel declines, while collagen content, including fibrosis, relatively increases.

Disc degeneration, which involves matrix, collagen and aggrecan, usually begins with annular tears or alterations in the endplate nutritional pathways by mechanical or pathophysiological means. However, the disc ultimately fails for cellular reasons. As a person ages, the discs in the spine go through a degenerative process that involves the gradual loss of the water holding capacity of the disc, referred to as desiccation. As a result of this loss of water, the disc space height may partially collapse, which may lead to chronic back pain disorders and/or leg pain as a result of the nerves being pinched.

Progressive injury and aging of the disc occurs normally in later life and abnormally after trauma or metabolic changes. In addition to the chemical effects on the free nerve endings as a source of discogenic pain, other degenerative factors may occur. Free nerve endings in the annular fibers may be stimulated by stretching as the disc degenerates, bulges, and circumferential delamination of annular fibers occurs. This condition may lead to a number of problems. It has been shown that a person's disc is typically taller in the morning when a person awakes. This phenomenon may be due in part to the reduction of body weight forces on the disc when lying in a recumbent position overnight that causes the disc height to restore. Therefore, the reduction of compressive forces on the disc may help to restore disc height.

As discussed above, as a person ages, the discs of the spine degenerate, and the disc space height collapses. Further, the ligaments and facets of the spine degenerate as well. These problems lead to a reduction in the foramenal height of the vertebrae, often causing central or lateral canal stenosis. The foramen is an opening through the vertebrae that allows the nerve from the spinal cord to pass through. Because the nerve passes through the foramen, the nerve will often get pinched as the disc height decreases, leading to various types of back pain. Further, these problems often lead to difficulty in walking. Additionally, the lateral canal stenosis causes the nerve to get pinched in the spinal canal. These conditions often lead to neurogenic claudication, where the patient typically responds by walking shorter distances, then sitting down, and then flexing the spine by leaning over or by walking with the aid of a device, which helps to flex the spine.

SUMMARY OF THE INVENTION

In accordance with the teachings of the present invention, a surgical screw is disclosed that includes a body portion that facilitates bone in-growth from a bone in which the screw is mounted so as to stabilize the screw in the bone. The body portion can have various configurations for facilitating bone in-growth, such as indentations, a roughened surface, such as by acid etching or sand blasting, specialized coatings, such as hydroxyapetite, sintered beads, machined channels, etc. Because the body portion of the screw facilitates bone growth, the screw will be more firmly mounted to the bone so as to have a greater integrity in response to movement of the bone. The type of surgical screw can be any surgical screw that will benefit from being better anchored in bone, such as pedicle screws, long bone screws, cervical fusion screws, tendon anchoring screws, etc.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a surgical screw having a body portion for facilitating bone in-growth to the screw is merely exemplary in nature, and is in no way intended to limit the invention or its applications or uses. For example, the surgical screw of the invention will have a number of different surgical applications, many of which are discussed below. However, as will be appreciated by those skilled in the art, other types of surgical screws for other applications not specifically mentioned may benefit from the bone growth to the screw.

Figure 1:
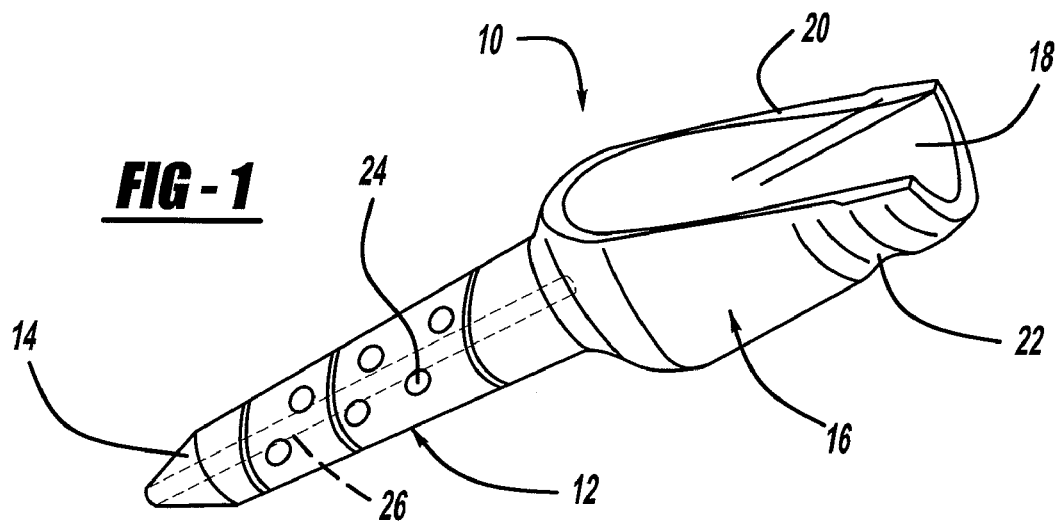
FIG. 1 is a perspective view of a pedicle screw employed in a motion preserving vertebral disc annular fibrosis tensioning and lengthening device of the invention.

FIG. 1 is a perspective view of a pedicle screw 10 for use in a vertebral disc annular fibrosis tensioning and lengthening device (FIG. 3) of the invention. The pedicle screw 10 includes a threaded and tapered body portion 12 having a tip 14. The body portion 12 includes a plurality of holes 24 that allow bone to grow therein when the screw 10 is threaded into the vertebral body so that the pedicle screw 10 is better anchored within the pedicle and the vertebra. The use of holes in the body portion of a pedicle screw to facilitate bone in-growth therein can be employed in other types of pedicle screws for other uses besides vertebral disc annular fibrosis tensioning and lengthening devices, such as spinal fusion pedicle screw and rod instrumentation, well known to those skilled in the art. The holes 24 can come in a variety of numbers, diameters and configurations. Bone in-growth into a lumbar screw based system allows for solid placement of a screw as part of a dynamic motion preserving posterior surgical system. In one non-limiting embodiment, the diameter of the body portion 12 is about 6.5 mm and the diameter of the holes is about 0.5 mm.

The pedicle screw 10 can include a bore 26 that extends through the body portion 12 to make it cannulated so that a K-wire (not shown) can extend therethrough to align the pedicle screw 10 to allow for percutaneous screw placement, as is well understood to those skilled in the art. The pedicle screw 10 further includes a screw head 16 having an extended cup shape defining a cavity 18. The cavity 18 includes an open side 20 for reasons that will become apparent from the discussion below. An annular recess 22 is formed around an outside of the head 16 also for reasons that will become apparent from the discussion below. The pedicle screw 10 can be made of any suitable material, such as titanium, as would be well understood to those skilled in the art.

Figure 2:
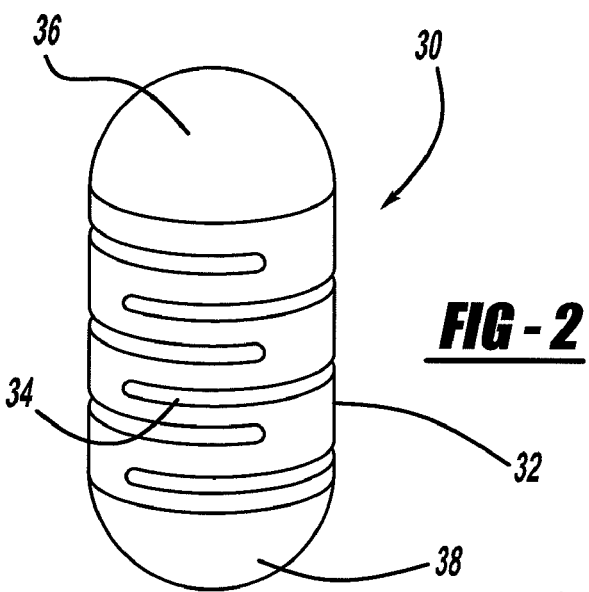
FIG. 2 is a perspective view of a spring employed in the vertebral disc annular fibrosis tensioning and lengthening device of the invention.

FIG. 2 is a perspective view of a spring 30 having a cylindrical body 32 that is also part of the vertebral disc annular fibrosis tensioning and lengthening device of the invention. A series of slots 34 are cut into the body portion 32, as shown, in an alternating configuration that allows the body portion 32 to be compressed and provide an expansive spring force. The spring 30 includes generally rounded ends 36 and 38 that are shaped to conform to the shape of the inner surface of the cavity 18 and allows for movement between the ends 36 and 38 of the spring 30 and the cavity 18 of the screw head 16. The spring 30 can be made of any suitable material for the purposes described herein, such as nitinol, which is a flexible metal having a memory. Other materials may also be suitable, such as a shape memory alloy. An example of a suitable alloy includes about 50% nickel and about 50% titanium. The ends 36 and 38 of the spring 36 and the cavity 18 of the screw head 16 can be made with materials to reduce wear debris, such as ceramic, cobalt, chrome, etc.

Figure 3:
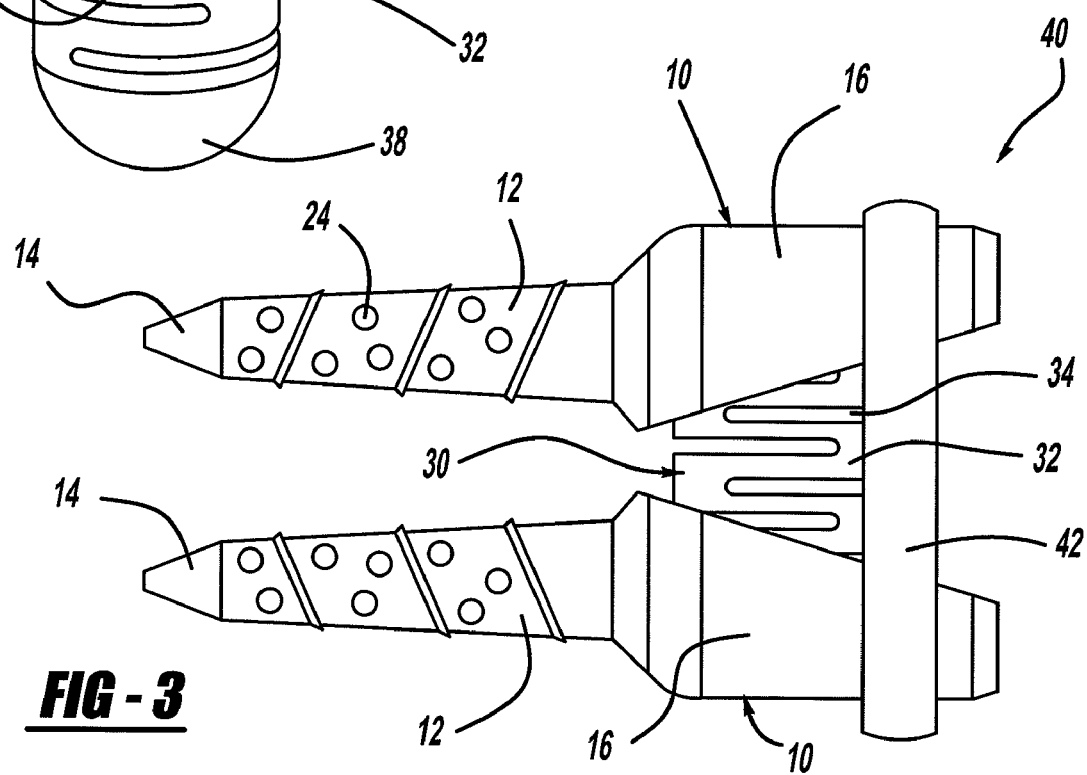
FIG. 3 is a side view of the vertebral disc annular fibrosis tensioning and lengthening device of the invention including two of the pedicle screws with the spring therebetween.
Figure 4:
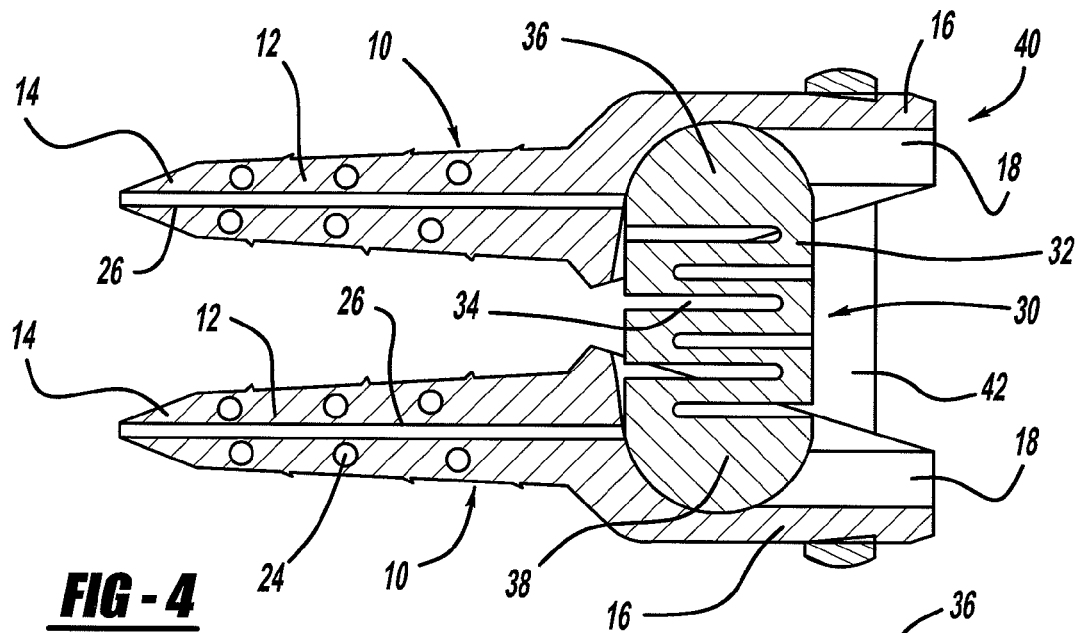
FIG. 4 is a cross-sectional side view of the vertebral disc annular fibrosis tensioning and lengthening device shown in FIG. 3.
Figure 5:
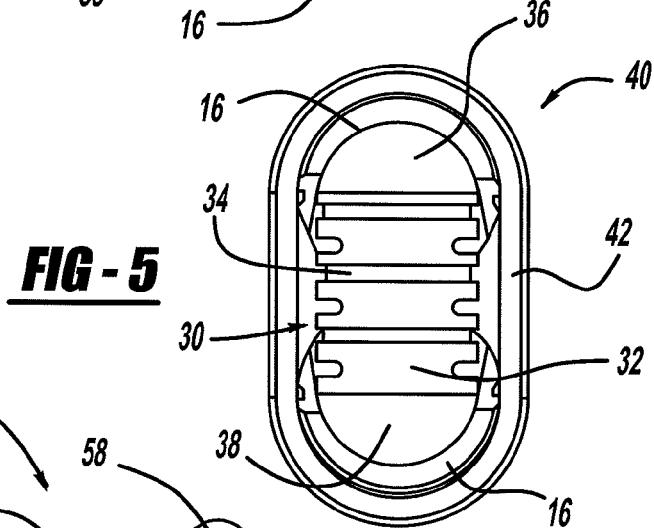
FIG. 5 is a top view of the vertebral disc annular fibrosis tensioning and lengthening device shown in FIG. 3.

FIG. 3 is a side view, FIG. 4 is a cross-sectional view, side view and FIG. 5 is a top view of a vertebral disc annular fibrosis tensioning and lengthening device 40, according to an embodiment of the present invention. The vertebral disc annular fibrosis tensioning and lengthening device 40 includes two of the pedicle screws 10 where the open sides 20 of the heads 16 face each other, as shown. The spring 30 is inserted into the cavities 18 of the heads 16 so that the ends 36 and 38 conform to the inner surface of the cavities 18. The inner surface of the cavities 18 and the ends 36 and 38 can be coated with a suitable low friction material, such as chrome, cobalt, ceramic, etc., to prevent or reduce wear particle formation as the spring 30 and the pedicle screws 10 rub against each other. Initially, the spring 32 is compressed so that it provides an expansive force to separate the pedicle screws 10. In one non-limiting embodiment, the expanded or relaxed length of the spring 30 is in the range of about 3 cm-4 cm, which is about the length from one pedicle screw head to the next. The diameter of the spring 32 can be any diameter suitable for the purposes described herein.

An oval posterior ring 42 is positioned within the recesses 22, and operates to maintain the spring 36 in place, and prevent the pedicle screws 10 from separating beyond a predetermined limit. Further, as the spring 30 causes the pedicle screws 10 to separate, the ring 42 maintains the top end of the pedicle screws 10 stationary to create a pivot and restore lordosis of the spine. The spring 30 operates as a compressible link and the posterior ring 42 operates as a rigid link.

Figure 6:
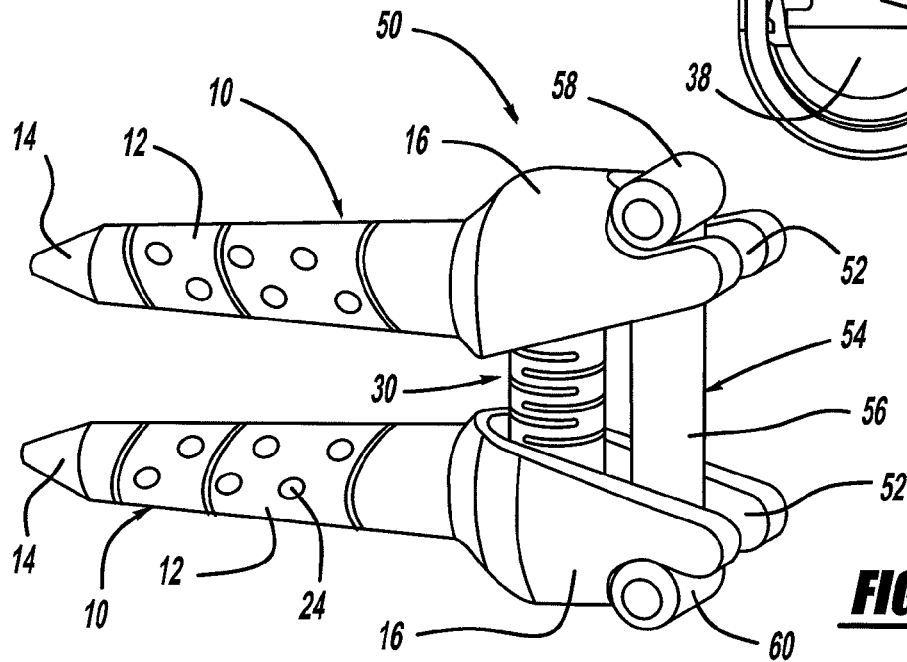
FIG. 6 is a perspective view of a vertebral disc annular fibrosis tensioning and lengthening device, according to another embodiment of the present invention.

FIG. 6 is a perspective view of a vertebral disc annular fibrosis tensioning and lengthening device 50, according to another embodiment of the present invention, where like elements to the vertebral disc annular fibrosis tensioning and lengthening device 40 are identified by the same reference numeral. In this embodiment, the heads 16 of the pedicle screws 10 include a slot 52. The ring 42 is replaced with a dumbbell member 54 including a cylindrical body portion 56 and end portions 58 and 60. The body portion 56 extends through the slots 52 so that the end portions 58 and 60 are positioned on outside sides of the heads 16, and also operates to limit the expansion of the pedicle screws 10 and control the posterior aspects of the screws 10.

Figure 7:
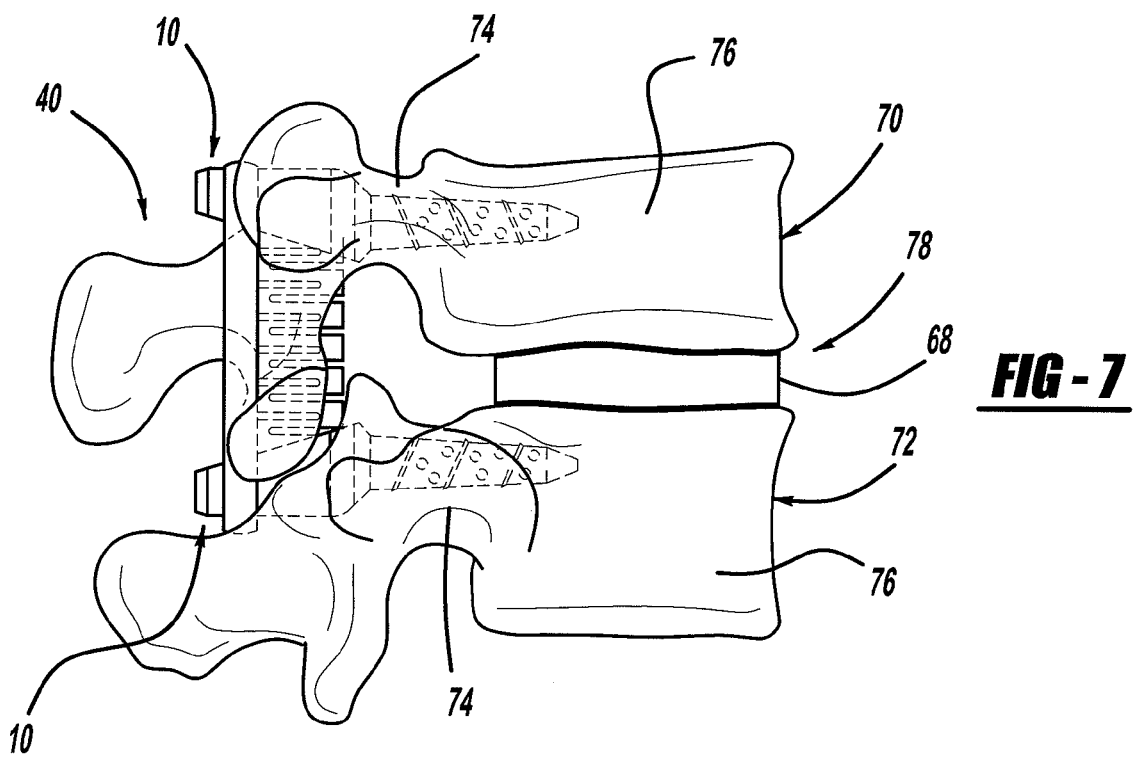
FIG. 7 is a side view showing a vertebral disc annular fibrosis tensioning and lengthening device of the invention inserted within adjacent vertebrae.
Figure 8:
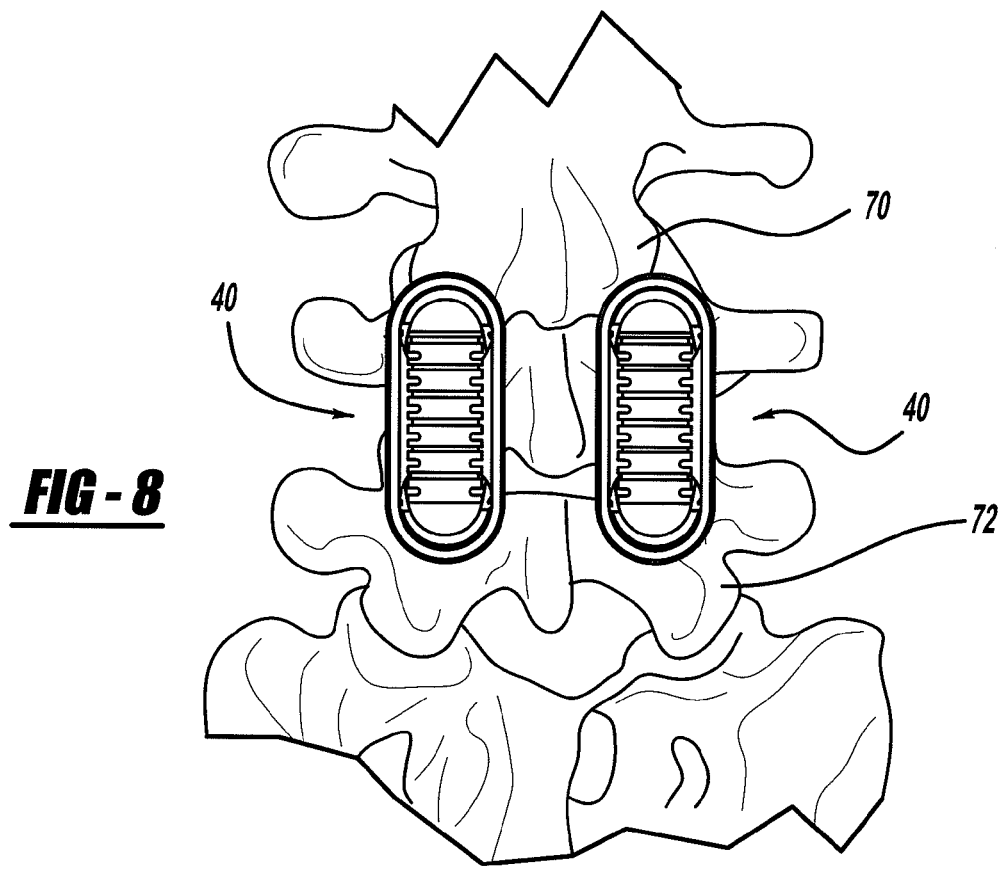
FIG. 8 is a top view of two vertebral disc annular fibrosis tensioning and lengthening devices of the invention inserted within the adjacent vertebrae.

FIG. 7 is a side view and FIG. 8 is a top view of two of the vertebral disc annular fibrosis tensioning and lengthening devices 40 coupled to two adjacent lumbar vertebra 70 and 72 having a disc 68 therebetween. The pedicle screws 10 are threaded through pedicles 74 of the vertebra 70 and 72 and into the vertebral body 76. Once the pedicle screws 10 are in place, then the spring 30 is positioned within the cavities 18 under compression, as discussed above. As the spring bias forces the vertebra 70 and 72 apart, the height of a disc space 78 between the vertebra 70 and 72 increases and is restored. Further, as the height of the disc space 78 increases, the disc 68 is able to regenerate due to reduced sheer or compressive forces applied to the disc 68. The device 40 creates a controlled distraction force and distraction distance on the annulus fibrosis and a controlled dynamic motion of the vertebra. Further, the device 40 allows motion of the spine while maintaining the stress tension effect on the disc 68. Particularly, the device 40 provides a tension force across a compromised vertebral disc providing a distractive force to elicit the stress tension effect on the annulus fibrosis. The pedicle screws and links therebetween are arranged in a parallelogram shape to provide the desired distraction. Because most systems work like a hinge, the front or anterior portion of the disc moves much more than the back or posterior portion of the disc thus helping to restore lodsis of the spine. In one non-limiting embodiment, the motion pathway is an arc of a radius much longer than the pedicle screw length. Although the device 40 is shown coupled to adjacent vertebra, the device 40 can extend across any suitable number of vertebrae to increase the disc space of more than one disc.

Any suitable surgical procedure for placing the pedicle screws 10 can be used, including minimally invasive surgical procedures by making the pedicle screws 10 cannulated. In one known process of percutaneous pedicle screw instrumentation, a Jamshidi needle is used to dock on to the junction of the vertebrae between the facet complex and the transverse process of the vertebra. Gentle taps with a mallet cause the Jamshidi needle to be advanced through the pedicle 74, making sure not to cross the medial border of the pedicle 74, which can result in nerve root injury, until the junction between the pedicle base and the vertebral body is reached. Fluoroscopic visualization into the anterior posterior and lateral planes of the vertebra is used to see the orientation of the Jamshidi needle. The correct trajectory of the Jamshidi needle should place the tip of the needle in the center of the pedicle in the anterior posterior view when the tip of the Jamshidi needle lies at the pedicle vertebral body junction in the lateral view.

Once the junction between the base of the pedicle wall and the vertebral body is reached, the Jamshidi needle can be directed in a more medial fashion. The Jamshidi needle is typically passed to about one-half the depth of the vertebral body, and then a K-wire is passed down the Jamshidi needle and into the vertebral body a little farther to seat it into the bone. The Jamshidi needle is then removed. A series of cannulated muscle dilators are then passed over the K-wire to prevent the soft tissue from going into the threads of the tap. The pedicle is tapped and a cannulated pedicle screw is then passed down the largest diameter dilator, and threaded down the pedicle into the vertebral body.

Although a specific type of spring has been described above for the vertebral disc annular fibrosis tensioning and lengthening device, the present invention contemplates any suitable linearly expandable link suitable for the purposes described herein. The link exerts a force creating a stress tension effect within the disc allowing it to regenerate according to Wolffs law. The link also allows parallel distraction of the disc, distraction along the coronal plane of the disc tissue, puts the annulus fibrous in tension and provides torsional rotation of the vertebral construct. Further, the pedicle screws can be replaced with any suitable mounting member. By a more general description, the vertebral disc annular fibrosis tensioning and lengthening device includes a caudle vertebral body attachment member and a cephelad vertebral body attachment member having a non-rigid interconnection member therebetween that creates the tension stress effect on the annulus fibrosis. The posterior ring 42 acts as a rigid member coupled between the attachment members that also operates to provide the distractive force.

Figure 9:
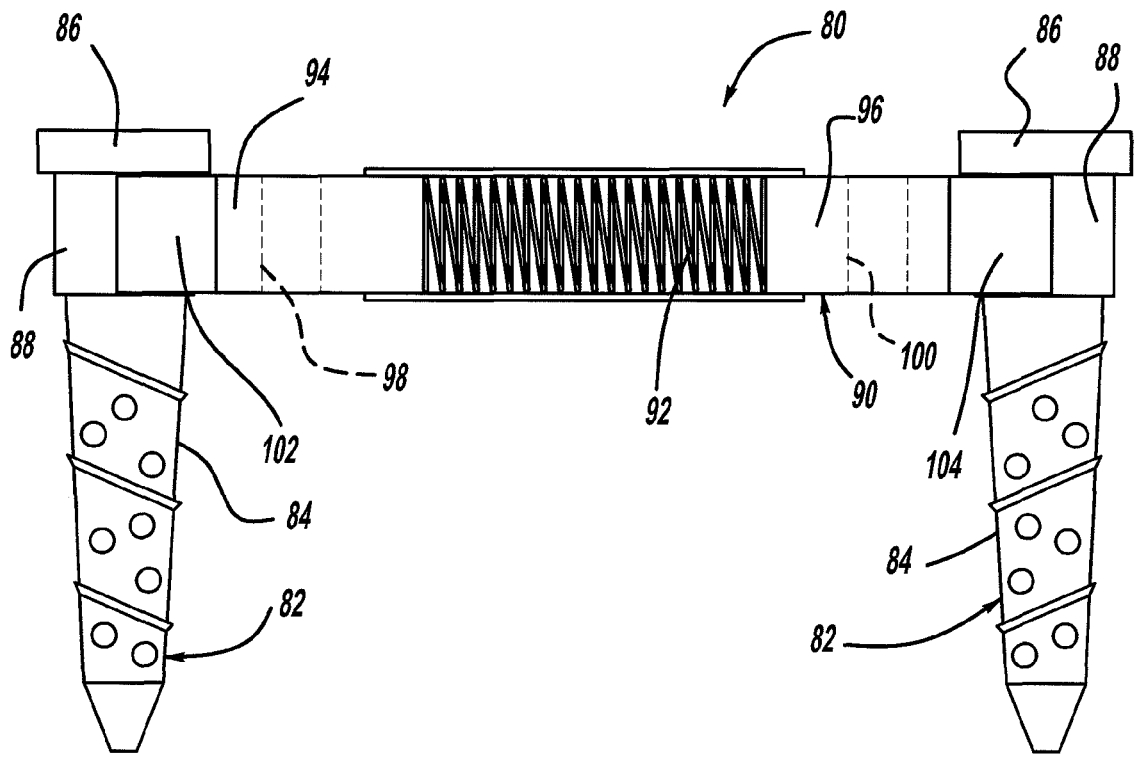
FIG. 9 is a side view of a vertebral disc annular fibrosis tensioning and lengthening device, according to another embodiment of the present invention.
Figure 10:
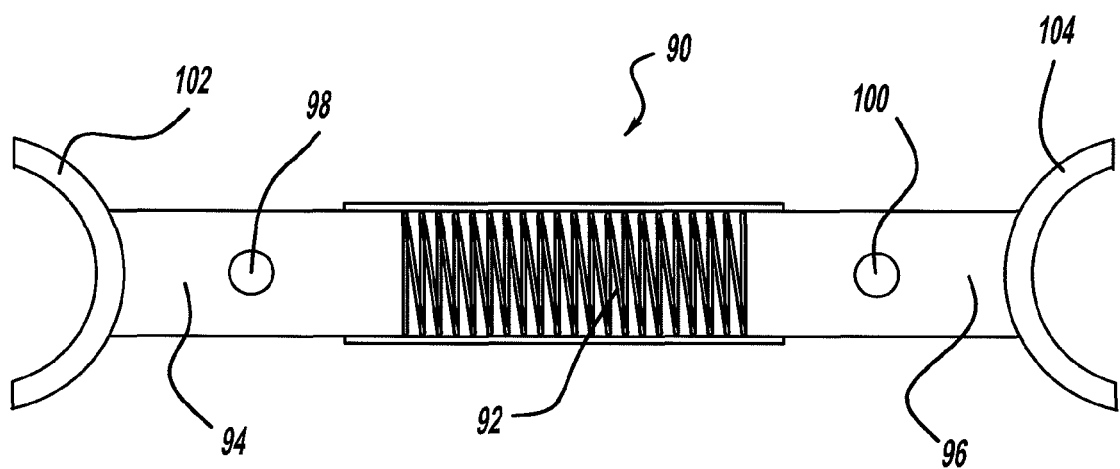
FIG. 10 is a top view of a spring member for the vertebral disc annular fibrosis tensioning and lengthening device shown in FIG. 9.

FIG. 9 is a side view of a vertebral disc annular fibrosis tensioning and lengthening device 80, according to another embodiment of the present invention. The device 80 includes pedicle screws 82 each having a screw body 84 and a screw head 86. An annular mounting portion 88 is provided between the screw head 86 and the screw body 84. The device 80 also includes a spring member 90 having a spring 92 and end plates 94 and 96. FIG. 10 is a top view of the spring member 90. The spring 92 can be any suitable spring, such as a helical spring. Holes 98 and 100 are provided through the end plates 94 and 96, respectively. A U-shaped coupling member 102 is attached to the end plate 94 and a U-shaped coupling member 104 is attached to the end plate 96. The U-shaped coupling members 102 and 104 have a size that conforms to the diameter of the annular mounting portion 88. The surgeon will use a suitable tool (not shown) that is inserted in the holes 98 and 100 to compress the spring 92 and position the U-shaped coupling members 102 and 104 around the annular mounting portions 88 so as to provide a separation force to the pedicle screws 82 for the reasons discussed above.

As discussed above, the pedicle screws 10 include the holes 24 for facilitating bone growth therein. Particularly, the holes 24 provide an opening in which bone material can grow. Such a concept eliminates or reduces the halo around the known pedicle screws that may occur and reduce the joining of the screw to the bone. The halo effect around pedicle screws is often seen in non-union spine fusion cases. This haloing occurred in spite of the screw threads that help anchor the screw to the bone. With the holes 24, the screw 10 will act more like natural bone and increase the integrity of the bonding between the screw and the vertebra, and allows for permanent fixation of the motion preserving posterior portion of the system.

The holes 24 are one example for accepting bone in-growth in a surgical screw, and provide better support to the bone in addition to the screw threads. Other configurations can also be employed for pedicle screws, and for other screws permanently placed in a bony structure to provide bone interdigitation. Suitable examples include an non-smooth or porous surface on the screw body, interdigitation cavities formed by the addition of sintered beads on the outside of the screw body, interdigitation cavities formed by laser processing, interdigitation cavities formed by machining grooves, a roughened surface provided by sand blasting, a hydroxyl appetite coating, etc. Further, the screws are not limited to pedicle screws, but can be screws for other surgical applications, such as maxio-facial applications, hip fractures, podiatric fusions and fraction repair, periarticular fracture fixation, arthroplasty device anchoring, long bone fracture repair, cervical fusion construct anchoring, tendon anchoring, etc.

Figure 11:
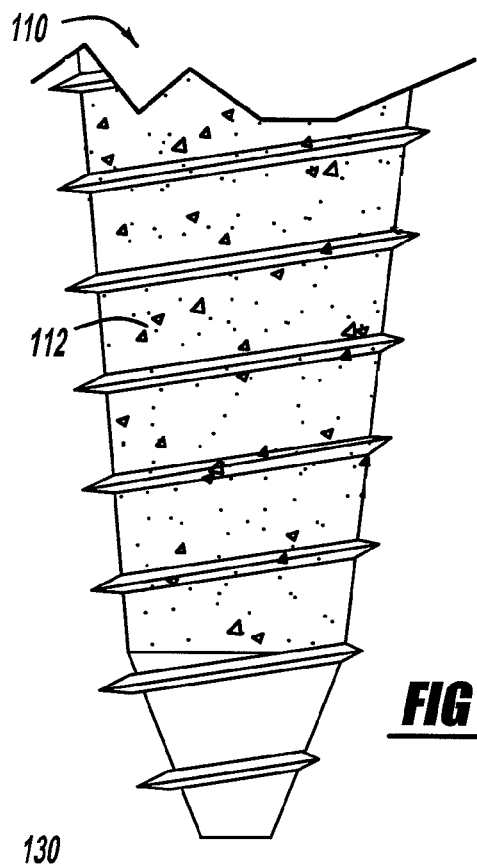
FIG. 11 is a broken-away side view of a body portion of a surgical screw including a roughened surface for facilitating bone in-growth to the screw, according to an embodiment of the present invention.

FIG. 11 is a broken-away side view of a body portion 110 of a surgical screw, according to an embodiment of the present invention. The body portion 110 includes a non-smooth or roughened surface 112 that operates to facilitate bone in-growth to the screw once the screw is surgically implanted in the bone. The roughened surface 112 can be provided by any suitable method that would be selected depending on the desired degree of roughness of the surface 112, the type of material of the body portion 110, the extent of the bone in-growth desired, etc. For example, the roughened surface 112 can be provided by acid etching, laser deformation, abrasive media blasting, such as sand blasting, etc. Also, the roughened surface 112 can be provided by depositing a mixture of substances on the body portion 110, where one of the substances is a leachable material so that when the body portion 130 is dipped in a suitable etchant, the leachable material will be removed from the surface creating the roughened surface 112.

Figure 12:
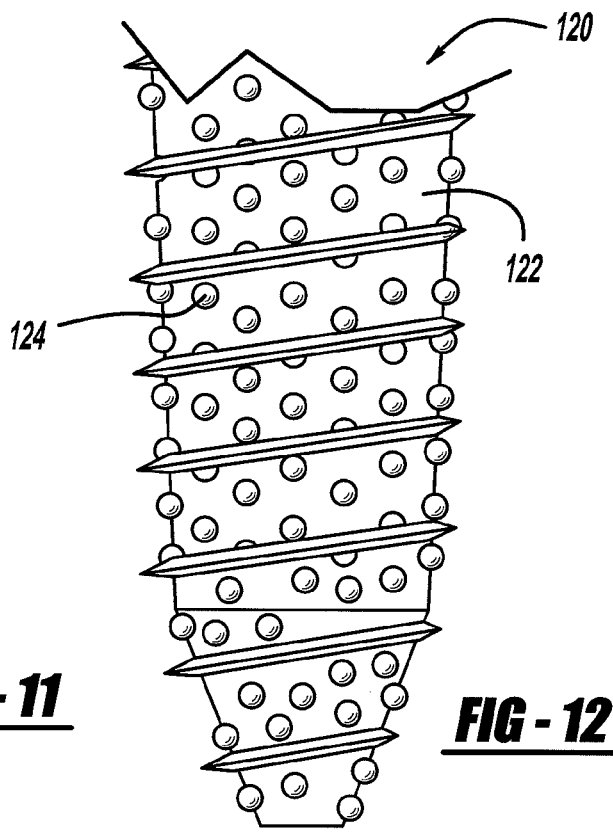
FIG. 12 is a broken-away side view of a body portion of a surgical screw including sintered beads for facilitating bone in-growth to the screw, according to another embodiment of the present invention.

FIG. 12 is a broken-away side view of a body portion 120 of a surgical screw, according to another embodiment of the present invention. A plurality of sintered beads 124 are formed to the body portion 120, where the sintered beads 124 facilitate bone growth to the screw once the surgical screw is surgically implanted in the bone. The number of the beads 124, the size of the beads 124, the material of the beads 124, etc. would depend on the particular application, surgical procedure, desired bone in-growth facilitation, etc. The sintered beads 124 can be formed to the surface 122 by any suitable sintering process.

Figure 13:
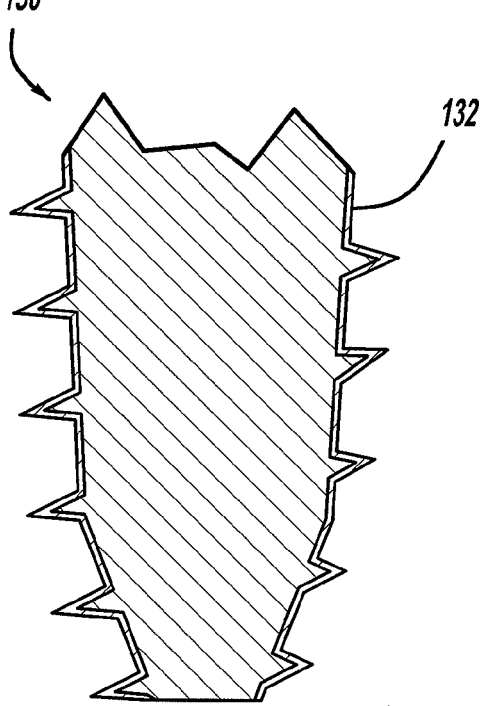
FIG. 13 is a broken-away cross-sectional view of a body portion of a surgical screw including an outer layer for facilitating bone in-growth to the screw, according to another embodiment of the present invention.

FIG. 13 is a broken-away, cross-sectional view of a body portion 130 of a surgical screw, according to another embodiment of the present invention. The body portion 130 includes an outer layer 132 that is made of a suitable material for facilitating bone in-growth. In one non-limiting embodiment, the outer layer 132 is hydroxyapetite, which is a mineral that is the principal storage form of calcium and phosphorous in bone. Therefore, the hydroxyapetite is conducive with the natural bone for providing a strong bond therebetween.

Figure 14:
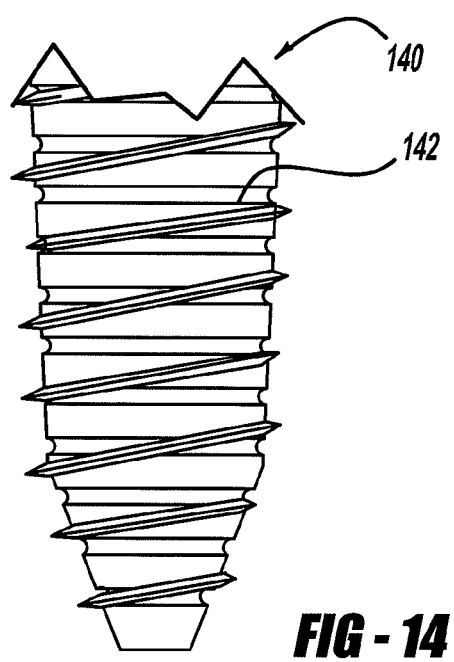
FIG. 14 is a broken-away side view of a body portion of a surgical screw including channels for facilitating bone in-growth to the screw, according to another embodiment of the present invention.

FIG. 14 is a broken-away side view of a body portion 140 of a surgical screw, according to another embodiment of the present invention. In this embodiment, channels 142 are formed, such as by sawing, in the outer surface of the body portion 140 to provide indentations that facilitate bone in-growth to the screw. The channels 142 are by way of a non-limiting example in that any machined indentations that facilitate bone in-growth can be provided.

Figure 15:
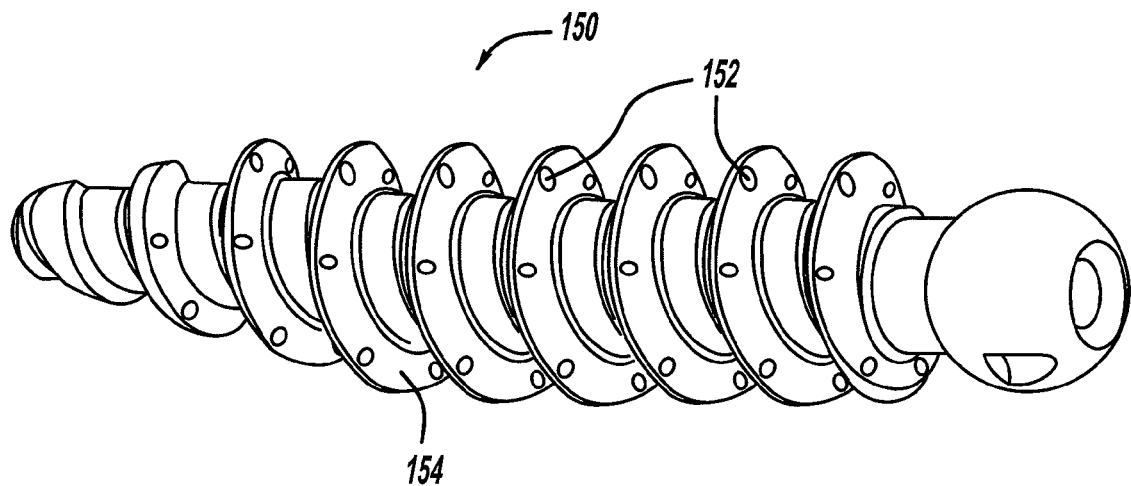
FIG. 15 is a perspective view of a surgical screw including axial holes within screw threads for facilitating bone in-growth to the screw, according to another embodiment of the present invention.

FIG. 15 is a perspective view of a surgical screw 150 including axial holes 152 extending through screw threads 154 for facilitating bone in-growth to the screw 150, according to another embodiment of the present invention.

Figure 16:
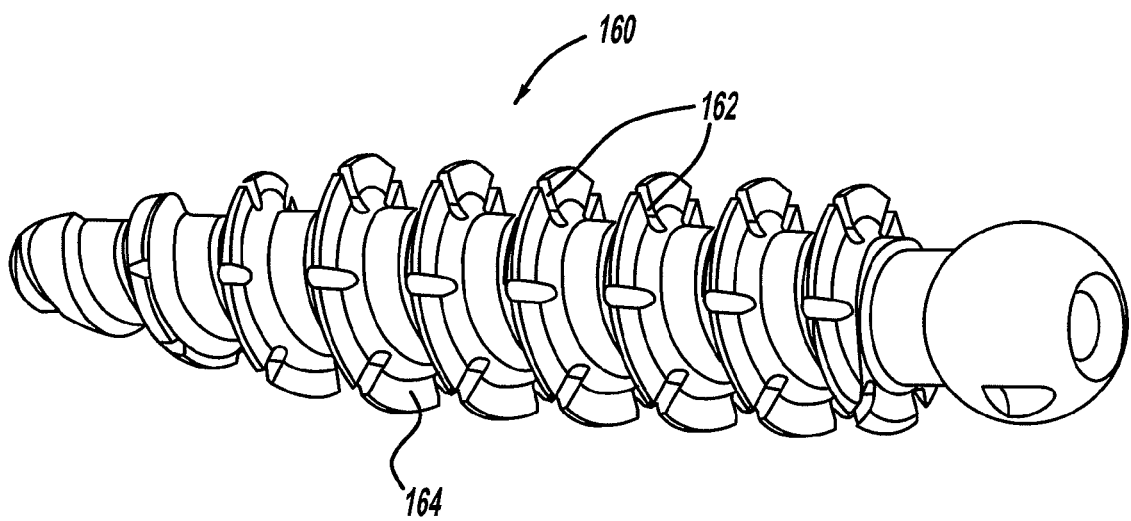
FIG. 16 is a perspective view of a surgical screw including radial slots within screw threads for facilitating bone in-growth to the screw, according to another embodiment of the present invention.

FIG. 16 is a perspective view of a surgical screw 160 including radial slots 162 circumferentially disposed around screw threads 164 for facilitating bone in-growth to the screw 160, according to another embodiment of the present invention. In this embodiment, the slots 162 extend partially into the major diameter of the screw 160.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A surgical screw comprising a head portion and a body portion, said body portion including a textured surface other than screw threads that facilitates bone in-growth to the screw so that the screw is more rigidly mounted to bone, wherein the body portion includes a roughened surface for facilitating bone in-growth, and wherein the roughened surface is formed by depositing two or more materials onto the body portion and leaching out one of the materials.

2. The screw according to claim 1 wherein the body portion includes an outer layer of hydroxyapetite.

3. The screw according to claim 1 wherein the body portion includes a plurality of spaced apart grooves.

4. The screw according to claim 1 wherein the body portion includes holes for facilitating bone in-growth.

5. The screw according to claim 4 wherein the body portion includes screw threads, said holes being formed axially through the screw threads.

6. The screw according to claim 1 wherein the body portion includes screw threads, said screw threads including a plurality of circumferentially disposed slots for facilitating bone in-growth.

7. The screw according to claim 1 wherein the screw is a pedicle screw.

8. The screw according to claim 1 wherein the screw is selected from the group consisting of maxio-facial application screws, hip fracture screws, podiatric fusion screws, fraction repair screws, periarticular fracture fixation screws, arthroplasty device anchoring screws, long bone fracture repair screws, cervical fusion construct anchoring screws and tendon anchoring screws.

9. A pedicle screw for spinal fusion surgery, said screw comprising a head portion and a body portion, said body portion including a plurality of openings that facilitate bone growth to the screw so that the screw is more rigidly mounted to the vertebra, wherein the openings are formed by depositing two or more materials onto the body portion and leaching out one of the materials.

10. The screw according to claim 9 wherein the body portion includes screw threads, said screw threads including a plurality of circumferentially disposed slots for facilitating bone in-growth.

* * * * *